US007361481B2

(12) United States Patent
Meikle et al.

(10) Patent No.: US 7,361,481 B2
(45) Date of Patent: Apr. 22, 2008

(54) DIAGNOSIS OF LYSOSOMAL STORAGE DISORDERS USING SAPOSINS AND OTHER MARKERS

(75) Inventors: Peter John Meikle, Redwood Park (AU); John Joseph Hopwood, Stonyfell (AU); Bryan Gordon Winchester, Surrey (GB)

(73) Assignee: Women's and Children's Hospital, North Adelaide (AU)

( * ) Notice: Subject to any disclaimer, the term of this patent is extended or adjusted under 35 U.S.C. 154(b) by 141 days.

(21) Appl. No.: 10/973,189

(22) Filed: Oct. 26, 2004

(65) Prior Publication Data

US 2005/0142590 A1 Jun. 30, 2005

Related U.S. Application Data

(62) Division of application No. 09/936,957, filed on Jan. 9, 2002.

(30) Foreign Application Priority Data

Apr. 9, 1999 (GB) ................................. 9908190.3

(51) Int. Cl.
*G01N 33/00* (2006.01)

(52) U.S. Cl. .................................................. 435/7.93

(58) Field of Classification Search ...... 435/7.91–7.95, 435/4, 287.1, 287.2, 287.9, 7.4; 436/518
See application file for complete search history.

(56) References Cited

U.S. PATENT DOCUMENTS

| | | | | |
|---|---|---|---|---|
| 3,881,993 A | * | 5/1975 | Freake et al. | 435/287.7 |
| 5,344,758 A | * | 9/1994 | Krilis et al. | 435/7.1 |
| 5,501,957 A | | 3/1996 | Dennis et al. | |
| 6,007,865 A | * | 12/1999 | Cerami et al. | 426/656 |
| 6,118,045 A | * | 9/2000 | Reuser et al. | 800/14 |
| 6,121,055 A | * | 9/2000 | Hargreaves | 436/526 |

FOREIGN PATENT DOCUMENTS

AU 29906/92 A 6/1993

OTHER PUBLICATIONS

Lin et al., "Study of Alpha-D Glycosidase activity in patients with Pompe's Disease", Taiwan yixuehui zazhi, (1986), vol. 85, No. 8, pp. 30-34.*
Griffiths et al., "Plasma acid hydrolases in normal adults and children and in patients with some lysosomal storage diseases", Clinica Chimica Acta, (1978), vol. 90, No. 2, pp. 129-141.*
O'Brian et al., "Saposin proteins: structure, function, and role in human lysosomal disorders," *FASEB J.*, 5(3):301-308 (1991).
Kishimoto et al., "Saposins: structure, function, distribution, and molecular genetics," *J. Lipid Research*, 33:1255-1267 (1992).
Meikle et al., "Diagnosis of lysosomal storage disorders: evaluation of lysosome-associated membrane protein LAMP-1 as a diagnostic marker," *Clinical Chemistry*, 43(8):1325-1335 (1997).

Aerts JM, Donker-Koopman WE, van der Vliet MK, Jonsson LM, Ginns EI, Murray GJ, Barranger JA, Tager JM, Schram AW. The occurrence of two immunologically distinguishable beta-glucocerebrosidases in human spleen. Eur J Biochem. Aug. 1, 1985;150(3):565-74.

Alexander D, Dudin G, Talj F, Bitar F, Deeb M, Khudr A, Abboud M, Der Kaloustian VM. Five related Lebanese individuals with high plasma lysosomal hydrolases: a new defect in mannose-6-phosphate receptor recognition? Am J Hum Genet. Sep. 1984;36(5):1001-14.

Baghdiguian S, Boudier JA, Boudier JL, Fantini J. Co-localization of suramin and serum albumin in lysosomes of suramin-treated human colon cancer cells. Cancer Lett. Mar. 29, 1996;101(2):179-84.

Brooks DA, McCourt PA, Gibson GJ, Hopwood JJ. Immunoquantification of the low abundance lysosomal enzyme N-acetylgalactosamine 4-sulphatase. J Inherit Metab Dis. 1990;13(1):108-20.

Burkhardt JK, Wiebel FA, Hester S, Argon Y. The giant organelles in beige and Chediak-Higashi fibroblasts are derived from late endosomes and mature lysosomes. J Exp Med. Dec. 1, 1993;178(6):1845-56.

Chamberlain P, Compston J, Cox TM, Hayman AR, Imrie RC, Reynolds K, Holmes SD. Generation and characterization of monoclonal antibodies to human type-5 tartrate-resistant acid phosphatase: development of a specific immunoassay of the isoenzyzme in serum. Clin Chem. Oct. 1995;41(10):1495-9.

Coleman, P. Effects of amino acid sequence changes on antibody-antigen interactions. Research In Immunology. 1994; 145:33-36.

Conary JT, Hasilik A, von Figura K. Synthesis and stability of steroid sulfatase in fibroblasts from multiple sulfatase deficiency. Biol Chem Hoppe Seyler. Apr. 1988;369(4):297-302.

Dahlgren C. Carlsson SR, Karlsson A, Lundqvist H, Sjolin C. The lysosomal membrane glycoproteins Lamp-1 and Lamp-2 are present in mobilizable organelles, but are absent from the azurophil granules of human neutrophils. Biochem J. Oct. 15, 1995:311 ( Pt 2):667-74.

Gatti R, Lombardo C, Filocamo M, Borrone C, Porro E. Comparative study of 15 lysosomal enzymes in chorionic villi and cultured amniotic fluid cells. Early prenatal diagnosis in seven pregnancies at risk for lysosomal storage diseases. Prenat Diagn. Sep.-Oct. 1985;5(5):329-36.

(Continued)

*Primary Examiner*—Ann Y. Lam
(74) *Attorney, Agent, or Firm*—Jackson Walker L.L.P.

(57) ABSTRACT

Methods for assaying a lysosomal enzyme activity present in a blood sample obtained from a patient. The method combines the blood or plasma sample in a buffer with at least one binding reagent capable of reacting with alpha-glucosidase present in the blood sample to form an enzyme reagent complex. The lysosomal enzyme activity present in the blood sample is then determined from the enzyme reagent complex formed and compared to a mean level of alpha-glucosidase in a control population of individuals not having a lysosomal storage disease.

5 Claims, 4 Drawing Sheets

OTHER PUBLICATIONS

Griffiths PA, Milsom JP, Lloyd JB. Plasma acid hydrolases in normal adults and children, and in patients with some lysosomal storage diseases. Clin Chim Acta. Dec. 1, 1978;90(2):129-41.

Hua CT, Hopwood JJ, Carlsson SR, Harris RJ, Meikle PJ. Evaluation of the lysosome-associated membrane protein LAMP-2 as a marker for lysosomal storage disorders. Clin Chem. Oct. 1998;44(10):2094-102.

Karageorgos LE, Isaac EL, Brooks DA, Ravenscroft EM, Davey R, Hopwood JJ, Meikle PJ. Lysosomal biogenesis in lysosomal storage disorders. Exp Cell Res. Jul. 10, 1997;234(1):85-97.

Kleiman FE, de Kremer RD, de Ramirez AO, Gravel RA, Argarana CE. Sandhoff disease in Argentina: high frequency of a splice site mutation in the HEXB gene and correlation between enzyme and DNA-based tests for heterozygote detection. Hum Genet. Sep. 1994;94(3):279-82.

Lovell KL, Kranich RJ, Cavanagh KT. Biochemical and histochemical analysis of lysosomal enzyme activities in caprine beta-mannosidosis. Mol Chem Neuropathol. Jan. 1994;21(1):61-74.

McCabe NR, Biliter W, Dawson G. Preferential inhibition of lysosomal beta-mannosidase by sucrose. Enzyme. 1990;43(3):137-45.

Michelakakis H, Dimitriou E, Van Weely S, Boot RG, Mavridou I, Verhoek M, Aerts JM. Characterization of glucocerebrosidase in Greek Gaucher disease patients: mutation analysis and biochemical studies. J Inherit Metab Dis. 1995;18(5):609-15.

Paschke E, Trinkl G, Erwa W, Pavelka M, Mutz I, Roscher A. Infantile type of sialic acid storage disease with sialuria. Clin Genet. May 1986;29(5):417-24.

Prence EM, Natowicz MR. Diagnosis of alpha-mannosidosis by measuring alpha-mannosidase in plasma. Clin Chem. Apr. 1992;38(4):501-3.

Renlund M. Clinical and laboratory diagnosis of Salla disease in infancy and childhood. J Pediatr. Feb. 1984;104(2):232-6.

Renlund M, Chester MA, Lundblad A, Aula P, Raivio KO, Autio S, Koskela SL. Increased urinary excretion of free N-acetylneuraminic acid in thirteen patients with Salla disease. Eur J Biochem. Nov. 1, 1979;101(1):245-50.

Renlund M, Aula P, Raivio KO, Autio S, Sainio K, Rapola J, Koskela SL. Salla disease: a new lysosomal storage disorder with disturbed sialic acid metabolism. Neurology. Jan. 1983;33(1):57-66.

Renlund M, Kovanen PT, Raivio KO, Aula P, Gahmberg CG, Ehnholm C. Studies on the defect underlying the lysosomal storage of sialic acid in Salla disease. Lysosomal accumulation of sialic acid formed from N-acetyl-mannosamine or derived from low density lipoprotein in cultured mutant fibroblasts. J Clin Invest. Feb. 1986;77(2):568-74.

Rodriguez-Serna M, Botella-Estrada R, Chabas A, Coll MJ, Oliver V, Febrer MI, Aliaga A. Angiokeratoma corporis diffusum associated with beta-mannosidase deficiency. Arch Dermatol. Oct. 1996;132(10):1219-22.

Sandoval IV, Chen JW, Yuan L, August JT. Lysosomal integral membrane glycoproteins are expressed at high levels in the inclusion bodies of I-cell disease fibroblasts. Arch Biochem Biophys. May 15, 1989;271(1):157-67.

Tager JM. Biosynthesis and efficiency of lysosomal enzymes. TIBS. 1985;10(8):324-326.

Waheed A, Hasilik A, von Figura K. Enhanced breakdown of arylsulfatase A in multiple sulfatase deficiency. Eur J Biochem. Apr. 1, 1982;123(2):317-21.

Whitley CB, Belani KG, Chang PN, Summers CG, Blazar BR, Tsai MY, Latchaw RE, Ramsay NK, Kersey JH. Long-term outcome of Hurler syndrome following bone marrow transplantation. Am J Med Genet. Apr. 15, 1993;46(2):209-18.

Yamaguchi K, Hayasaka S, Hara S, Kurobane I, Tada K. Improvement of tear lysosomal enzyme levels after treatment with bone marrow transplantation in a patient with I-cell disease. Ophthalmic Res. 1989;21(3):226-9.

Guo Y, He W, Boer AM, Wevers RA, De Bruijn AM, Groener JEM, Hiollak CEM, Aerts JMFG, Galjaard H, Van Diggelen OP. Elevated Plasma Chitotriosidase Activity in Various Lysosomal Storage Disorders. J. Inherited Metabolic Disease. 1995;18(6)717-722.

\* cited by examiner

Figure 1

Figure 2, Sheet 1

Figure 2, Sheet 2

(c)

(d)

Figure 3 Box plot of alpha-glucosidase levels in plasma from control and LSD affected individuals

DIAGNOSIS OF LYSOSOMAL STORAGE DISORDERS USING SAPOSINS AND OTHER MARKERS

CROSS-REFERENCE TO RELATED APPLICATIONS

This is a divisional application of prior U.S. patent application Ser. No. 09/936,957, filed Jan. 9, 2002, which claims priority to a U.S. Provisional Patent Application Ser. No. 60/124,864, filed Mar. 17, 1999, and GB 99 08190.3, filed Apr. 9,1999, the entire content of each of which is incorporated by reference.

BACKGROUND

Lysosomal storage disorder (LSDs) are a large family of genetic disorders that can lead to the manifestation of severe clinical symptoms. Although the frequency of each individual disease is relatively rare, the collective incidence of all lysosomal storage disorders is about 1 in 7000 newborns. This is greater than that of other diseases, such as phenylketonuria, for which newborn screening methods are available. Each lysosomal storage disorder results from a deficiency in a lysosomal enzyme, transporter or protein involved in lysosomal biogenesis or function [1]. The deficiency leads to the accumulation of substrates, normally degraded within the lysosome, and an increase in size and number of lysosomes within the cells.

Predominantly affecting young children, LSDs can be very severe with a wide range of clinical symptoms that depend on the particular genotype involved including mental retardation, skeletal abnormalities, organomegaly, corneal clouding and coarse facial features [2] [1]. In recent years treatments for several LSDs have become possible including drug therapy [3-5], bone marrow transplantation [2, 6], and enzyme replacement therapy [6, 7]. New treatment protocols are being developed with the increased knowledge of the underlying cause of the specific disorders, and the availability of animal models together with the development of new technologies. Animal models are of particular importance for the testing of new treatments such as enzyme replacement therapy [2, 6, 8, 9], and studies in animal models have also shown that maximum efficacy, in most cases, is achieved when treatment is given at an early stage of pathology [10, 11].

In most of the disorders, clinical pathology is not apparent at birth but presents in the first few years of life. For current and proposed therapies to achieve maximum efficacy it is important that the disorders are detected early, before the onset of irreversible pathology, particularly if there is central nervous system and/or bone pathology involvement. Thus, there is a need for screening methods for newborns, preferably screening methods that can detect all or most lysosomal disorders with a minimum number of assays. The present invention fulfils this and other needs.

DEFINITIONS

A patient is a subject, typically human, either living or subject to postmortem analysis, undergoing a diagnostic test to determine whether the patient has a disorder, susceptibility thereto, or above-normal risk thereof. A patient has a disease if the patient is currently showing symptoms thereof. A patient is susceptible to the disease if the patient is presently asymptomatic but has a genetic or other disposition to acquire the disease at a later time. A patient is at above normal risk of having the disease if the patient possesses a genetic or biochemical marker correlated with presence of the disease in a population of individuals. Some patients undergoing a diagnostic test are suspected of having the disease from symptoms, family history or other tests previously conducted. Other patients undergoing a diagnostic test have no known symptoms, or other risk factor for the disease, but undergo the test as a precautionary screening, optionally in conjunction with other tests.

A diagnostic test serves to indicate that a patient has a disorder being tested for, is susceptible to such a disorder, or has above normal risk of having such a disorder relative to the general population.

Unless the context requires otherwise, the word "comprise," or variations such as "comprises" or "comprising" imply the inclusion of a stated element or integer or group of elements or integers, but not the exclusion of any other element or integer or group of elements or integers.

Specific binding of a reagent with an analyte to form a complex means that the complex has a dissociation constant of less than micromolar.

SUMMARY OF THE CLAIMED INVENTION

The invention provides methods of diagnosing or monitoring a lysosomal storage disease in a patient. The methods entail measuring the level of at least one saposin in a tissue sample of the patient, the level providing an indication of the presence or absence or extent of the disorder in the patient. In some methods, the sample is a plasma sample. In some methods, presence of a disorder is indicated by a measured level of saposin exceeding a mean level of the saposin in a control population of individuals not having a lysosomal storage disease. In some methods, presence of a disorder is indicated when the measured level of saposin exceeds the 95th percentile level in the control population. In some methods, the patient is not known to have a lysosomal storage disorder before the measuring step. In some methods, the patient is less than one year old. In some methods, the patient is a foetus. The saposin detected in such methods can be any of saposin A, B, C or D, prosaposin, mRNA encoding any of these or subtypes of these saposins. In some methods, saposins are detected using an antibody as the diagnostic reagent. In some methods, the lysosomal storage disease is cystinosis, Fabry's disease, Niemann-Pick disease, Pompe's disease or Wolman's disease. Some methods also include a step of informing a patient, a parent or a guardian of the results of the presence of a lysosomal storage disease indicated by the measuring step.

The invention further provides methods of diagnosing or monitoring a lysosomal storage disorder in a patient in which the level of α-glucosidase is measured in a tissue sample from a patient. The level of the α glucosidase provides an indicator of the presence or extent of the disorder in the patient. In some methods, the sample is a plasma sample or whole blood sample. In some methods, the measuring step indicates presence of acid lipase disease, mannosidosis, mucopolysaccharidosis II (MPSII), MPS IIIA, MSD, mucolipidosis, N-P (A/B), N-P(C), Sandhoff, SAS or TSD B1 from an increased concentration of α-glucosidase relative to the mean level in a control population of individuals not having a lysosomal storage disease. In some methods, the measuring step indicates presence of MPS IVA or Pompe's disease from a decreased level of α glucosidase relative to the mean level in a control population of individuals not having lysosomal storage disease.

The invention further provides methods of diagnosing a lysosomal storage disease by measuring a level of a saposin, measuring a level of LAMP-1 or LAMP-2 and measuring a level of α glucosidase in the same or different tissue samples from a patient. Presence of increased levels of saposin, LAMP-1 or LAMP-2 and either increased or decreased levels of α glucosidase relative to corresponding levels in a control population of individuals not having a lysosomal storage disorder is an indicator of a lysosomal storage disorder.

The invention further provides diagnostic kits. Some such kits comprise a first reagent that binds to a LAMP and a second reagent that binds to a saposin. Some kits further comprise a third reagent that binds to α glucosidase.

The invention also provides methods of monitoring treatment of a lysosomal storage disease in a patient. Such methods entail determining a baseline level of a saposin in a tissue sample from a patient with a lysosomal storage disorder before treatment with an agent. The baseline level is then compared with a level in a sample obtained after the patient has been treated with the agent. A reduction in the level of saposin after treatment relative to the baseline indicates a positive treatment outcome.

The invention also provides methods of monitoring treatment of acid lipase disease, mannosidosis, MPSII, MPS IIIA, MSD, mucolipidosis, N-P (A/B), N-P(C), Sandhoff, SAS or TSD B1. Such methods entail determining a baseline level of α glucosidase in a tissue sample from the patient with the disorder before treatment with an agent. The baseline level is then compared with a level of the α glucosidase in a tissue sample from the patient with the disorder after treatment with the agent. A decrease relative to the baseline indicates a positive treatment outcome.

The invention also provides methods of monitoring a patient with galactosialidosis, MPS IVA or Pompe's disease. Such methods entail determining a baseline level of α glucosidase in a tissue sample from the patient with the disorder before treatment with the agent. The baseline level is then compared with a level of the α-glucosidase in a tissue sample from the patient after treatment with the agent. An increase relative to the baseline indicates a positive treatment outcome.

BRIEF DESCRIPTION OF THE DRAWINGS

FIG. 2. Box plots of saposin concentrations in plasma from control and LSD-affected individuals. Saposin concentrations were determined by using 0.25-2 μL plasma samples. N=number of samples used in each group. The line within the box is the median level, shaded areas below and above the median represent the $25^{th}$ and $75^{th}$ centiles, respectively, and bars represent the range. ○ depicts the outliers, and * denotes extreme outliers. Galact=galactosialidosis; GM I=GM I gangliosidosis; Mann=α-Mannosidosis; MLD=metachromatic leukodystrophy; MSD=Multiple Sulphatase Deficiency; NCL=Neuronal Ceroid Lipofuscinosis; N-P=Niemann-Pick disease; SAS=Sialic Acid Storage disease; TSD=Tay-Sachs disease.

FIG. 3 Box plot of α-glucosidase levels in plasma from control and LSD affected individuals Alpha-glucosidase concentrations were determined by using 5.0 μL plasma samples. N=number of samples used in each group. The line within the box is the median level, shaded areas below and above the median represent the $25^{th}$ and $75^{th}$ centiles, respectively, and bars represent the range. ○ depicts the outliers, and * denotes extreme outliers. Galact=galactosialidosis; GM I=GM I gangliosidosis; MLD=metachromatic leukodystrophy; MSD=Multiple Sulphatase Deficiency; N-P=Niemann-Pick disease; SAS=Sialic Acid Storage disease; TSD=Tay-Sachs disease. The Y axis has been expanded to highlight differences between the control and LSD patient

DETAILED DESCRIPTION

I. General

The invention provides methods of diagnosing patients for presence of lysosomal storage disorders. The methods work by detecting a biological marker correlated with at least one or a subset of such disorders. Some methods detect one or more naturally occurring polypeptides termed saposins. The presence of above normal levels of such polypeptides in a tissue sample from of a patient is correlated with several types of lysosomal disease including cystinosis, Fabry disease, Niemann-Pick disease (types A/B and C), Pompe's disease, Wolman disease, Krabbe disease, metachromatic leukodystrophy, and Tay-Sachs disease. Other methods entail determining the level of α-glucosidase in a tissue sample from a patient. Levels of α-glucosidase are depressed relative to normal levels in Pompe's disease. Levels of α-glucosidase are elevated relative to normal levels in acid lipase disease, mannosidosis, MPS II, MPS IIIA, multiple sulphatase deficiency, mucolipidosis, Niemann-Pick (A/B), Niemann-Pick (C), sialic acid storage disease or Sandhoff's disease, Tay-Sachs disease A/B.

The methods are suitable for large scale screening of recently born infants or foetuses for the presence of lysosomal storage disorders, optionally, in conjunction with additional biochemical and/or genetic markers of other disorders that may reside in newborns. The methods are also suitable for monitoring patients who have previously been diagnosed with a lysosomal storage disease, particularly their response to treatment. Methods of analysing of saposins and α-glucosidase can be performed in combination, optionally in further combination with detecting other biochemical markers correlated with lysosomal storage disorders, as described by WO 97/44668. Optionally, analysis of biochemical markers can also be combined with polymorphic analysis of genes encoding lysosomal enzymes for polymorphisms correlated with disease.

II. Lysosomal Storage Disorders

There are over thirty lysosomal diseases, each resulting from a deficiency of a particular lysosomal protein, usually as a result of genetic mutation; See, eg., Cotran et al., Robbins Pathologic Basis of Disease ($4^{th}$ ed. 1989) (incorporated by reference in its entirety for all purposes). The deficiency in the lysosomal protein usually results in harmful accumulation of a metabolite. For example, in Hurler's, Hunter's, Morquio's, and Sanfilippo's syndromes, there is an accumulation of mucopolysaccharides; in Tay-Sachs, Gaucher, Krabbe, Niemann-Pick, and Fabry syndromes, there is an accumulation of sphingolipids; and in fucosidosis and mannosidosis, there is an accumulation of fucosecontaining sphingolipids and glycoprotein fragments, and of mannose-containing oligosaccharides, respectively.

Glycogen storage disease type II (GSD II; Pompe's disease; acid maltase deficiency) is caused by deficiency of the lysosomal enzyme acid α-glucosidase (acid maltase). Three clinical forms are distinguished: infantile, juvenile and adult. Infantile GSD II has its onset shortly after birth and presents with progressive muscular weakness and cardiac failure. This clinical variant is fatal within the first two years of life. Symptoms in adult and juvenile patients occur later in life, and only skeletal muscles are involved. The patients eventually die due to respiratory insufficiency. Patients may exceptionally survive for more than six decades. There is a good correlation between the severity of the disease and the residual acid α-glucosidase activity, the activity being 10-20% of normal in late onset and less than 2% in early onset forms of the disease (see Hirschhom, The Metabolic and Molecular Bases of Inherited Disease (Schriver et al., eds., $7^{th}$ ed., McGraw-Hill, 1995), pp. 2443-2464).

There are more than 30 known genes encoding lysosomal enzymes including α-glucosidase, α L-iduronidase, iduronate-sulfate sulfatase, hexosaminidase A and B, ganglioside activator protein, arylsulfatase A and B, iduronate sulfatase, heparin N-sulfatase, galacto-ceramidase, α-galactosylceramidase A, sphingomyelinase, α-fucosidase, α-mannosidase, aspartylglycosamine amide hydrolase, acid lipase, N-acetyl-α-D-glucosamine-6-sulfate sulfatase, α- and β-galactosidase, β-glucuronidase, β-mannosidase, ceramidase, galactocerebrosidase, α-N-acetylgalactosaminidase, and protective protein and others. DNA clones containing the genomic or cDNA sequences of many of the known genes encoding lysosomal proteins are available. (Scott et al., Am. J. Hum. Genet. 47, 802-807 (1990); Wilson et al., PNAS 87, 8531-8535 (1990); Stein et al., J. Biol. Chem. 264, 1252-1259 (1989); Ginns et al., Biochem. Biophys. Res. Comm. 123, 574-580 (1984); Hoefsloot et al., EMBO J. 7, 1697-1704 (1988); Hoefsloot et al., Biochem. J. 272, 473479 (1990); Meyerowitz & Proia, PNAS 81, 5394-5398 (1984); Scriver et al., supra, part 12, pages 2427-2882 and references cited therein)) Other examples of genomic and cDNA sequences are available from GenBank.

III. Saposins

Saposins are small, heat-stable, glycoproteins of which there are four, termed saposins A, B, C and D. All four saposins are derived from a single 73 kD precursor protein called prosaposin. The mature saposins have specific roles in activating and enhancing the activities of their respective lysosomal hydrolases [15, 16]. Saposins are critical in the control of the glycosphingolipid flux through the lysosomal hydrolytic pathway [15] and genetic defects in sphingolipid hydrolases and/or saposins have been associated with the storage of sphingolipids. [17]. All saposins contain about 80 amino acids and show a high degree of sequence identity to each other. Each saposin contains six cysteine residues in nearly identical positions, all of which form three disulfide bridges providing hairpin type structures. Each saposin also contains N-glycoside type carbohydrate chains. They are linked to identical asparagine residue situated at the $21^{st}$ position from the N-terminal end of each saposins. Among the four saposins, only saposin A has an additional carbohydrate chain linked to the 42 asparagine residue. Structurally important proline residues are also conserved at nearly identical positions. In all, 13 amino acids are conserved in identical positions in each saposin domain. In addition, there are many amino acids of similar nature, especially hydrophobic amino acid residues, at the same position in each domain. Despite such similarity, they are immunologically distinguishable and functionally different. The saposins are well conserved among different animal species, including human, bovine, rat, pig, and even chicken.

Saposins are required for enzymic hydrolysis of certain sphingolipids by specific lysosomal hydrolases. Although saposins are highly homologous to each other, they show unique and distinct specificities. The first discovered saposin, saposin B, stimulates the hydrolysis reactions by arylsulfatase A, GM1 ganglioside β-galactosidase, and α-galactosidase A. Saposin C also catalyses this reaction, although it has less activity. Saposin D stimulates activities of sphingomyelinase and ceramidase. There are probably three distinct pools of prosaposin in human tissues: one for the lysosomal target, one for secretion, and one for targeting to plasma membrane.

As described in Example 1, elevated levels of saposins correlate positively with presence of several lysosomal storage disorders. Although any of the saposins, and the mRNA encoding the same, can be used as screening marker, saposins A, C and/or D are preferred because these saposins show the strongest correlations. Any or all of at least three mechanisms may explain the observed accumulation of saposins in tissue samples from LSD patients described in Example 1. First, the synthesis of saposins may be stimulated by the accumulation of either a defective enzyme or lipids as a compensatory mechanism. Second, saposins may be co-deposited with substrates that accumulate through lack of processing by a defective enzyme. Third, saposins may fail to be degraded through inability to interact with a nonfunctional lysosomal enzyme. The present invention is not, however, dependent on an understanding of mechanism.

IV. α-glucosidase

Acid α-glucosidase is the enzyme associated with the lysosomal storage disorder termed Pompe's disease. Alpha-glucosidase is initially synthesised in a precursor form of about 100-110 kD. (The apparent molecular weight or relative mobility of the precursor may vary somewhat depending on the method of analysis used, but will typically be within the range 95 kD and 120 kD.) The proteolytic processing of acid α-glucosidase is complex and involves a series of steps in addition to cleavage of the signal peptide taking place at various subpleural locations. Polypeptides are cleaved off at both the N and C terminal ends, whereby the specific catalytic activity is increased. The main species recognised are a 110/100 kD precursor, a 95 kD intermediate and 76 kD and 70 kD mature forms. (Hasidic et al., J. Biol. Chem. 255, 49374945 (1980); Ode Elferink et al., Eur. J. Biochem. 139, 489-495 (1984); Reuser et al., J. Biol. Chem. 260, 8336-8341 (1985); Hoefsloot et al., EMBO J. 7, 1697-1704 (1988)).

The present invention provides evidence that levels of acid α-glucosidase are depressed in Pompe's disease and in certain other lysosomal storage disorders. Conversely, levels of acid α-glucosidase are elevated in certain other lysosomal storage disorders including mannosidosis, MPS II, MPS IIIA, MSD, mucolipidosis, Nieman Pick (A/B), Nieman Pick (C), Sandhoff, SAS or Tay Sachs disease A/B. Therefore, acid a-glucosidase levels are a useful biochemical marker for screening for lysosomal storage disorders. The present methods detect each of the various molecular weight forms of acid a glucosidase, combinations thereof, and mRNA encoding acid α-glucosidase.

V. Other Biochemical Markers

WO 97/44668 describes a number of protein markers, including LAMP-1 and LAMP-2, that are correlated with lysosomal storage diseases. LAMP-1 and LAMP-2 are lysosomal membrane glycoproteins (Dahlgren et al., Biochem. J. 311, 667-674 (1995). LAMP-1 is a preferred marker. Elevated levels of LAMP-1 correlate with Gaucher's disease, galactosialidosis, GM1-gangliosidosis, I-cell disease, acid mannosidosis, MPS I, MPS II, MPS IIIA, MPS IIIB, MPS IIID, MPS IV A, MPS VI, multiple sulphatase deficiency, Sandhoff disease, sialic acid storage disease, and Tay-Sachs (AB) disease (13). Levels of LAMP-2 are also increased in many of the same LSDs as LAMP-1 [14] Several of the LSD's that are not correlated with LAMP-1 are correlated with saposin levels (See Table 1). Thus, combined screens for LAMP-1 and saposins identify more patients with lysosomal storage disorders than either screen alone.

VI. Tissue Samples

Samples for analysis can be obtained from any organ, tissue, fluid or other biological sample comprising lysosomes or their component proteins. A preferred tissue sample is whole blood and products derived therefrom, such as plasma and serum. Blood samples can be obtained from blood-spot taken from, for example, a Guthrie card. Other sources of tissue samples are skin, hair, urine, saliva, semen, faeces, sweat, milk, amniotic fluid, liver, heart, muscle, kidney and other body organs. Others sources of tissue are cell lines propagated from primary cells from a patient. Tissue samples are typically lysed to release the protein and/or nucleic acid content of cells within the samples. The protein or nucleic acid fraction from such crude lysates can then be subject to partial or complete purification before analysis.

Samples can be obtained from embryos, foetuses, neonatals, young infants or adults. Typically, samples are obtained from neonatals within a day, week, month or up to six months after birth. Foetal samples can be obtained in the form of, for example, amniotic fluid from the mother, or foetal blood. Amniotic fluid is preferably withdrawn from the womb of a pregnant woman using, for example, 20 or 22 gauge needles under continuous ultrasonic guidance. Methods for obtaining foetal blood are described by Daffos in The Unborn Patient-Prenatal Diagnosis and Treatment (Harrison et al. eds., W. B. Sanders, Philadelphia, Pa. 1991), ch. 11.

In some methods, multiple diagnostic tests for multiple markers are performed on the same patient. Typically, multiple tests are performed on different aliquots of the same tissue sample. However, multiple assays can also be performed on separate samples from the same tissue source, or on multiple samples from different tissue sources. For example, a test for one marker can be performed on a plasma sample, and a test for a second marker on a whole blood sample. In some methods, multiple samples are obtained from the same patient at different time points. In such methods, the multiple samples are typically from the same tissue, for example, all plasma.

VI. Protein Assay Formats

Polypeptide analytes such as saposins, α-glucosidase and LAMP-1 can be assayed by a binding assay using an antibody or other reagent with specific binding affinity for the analyte. In brief, a sample containing the analyte is incubated with an antibody or other binding reagent and the complex formed is detected and quantified. Conditions for incubating an antibody or other binding reagent with a test sample vary, depending upon the format employed in the assay, the detection methods employed and the type and nature of the binding reagent used in the assay. Any one of the commonly available immunological assay formats, for example radioimmunoassays, enzyme-linked immunosorbent assays (ELISA), diffusion-based Ouchterlony, rocket-gel immunoelectrophoresis or in situ immunoassays can be used.

Examples of such assay formats can be found in U.S. Pat. Nos. 3,791,932; 3,817,837; 3,839,153; 3,850,752; 3,850, 578; 3,853,987; 3,867,517; 3,879,262; 3,901,654; 3,935, 074; 3,984,533; 3,996,345; 4,034,074; and 4,098,876, 3,791,932; 3,839,153; 3,850,752; 3,879,262; and 4,034,074, 4,016,043, 4,424,279 and 4,018,653. The results can be qualitative, by simple observation of the visible signal or can be quantitated by comparison with a control sample containing known amounts of analyte. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. The antibodies used above can be monoclonal or polyclonal.

The substrate for use in solid phase assays is typically glass or a polymer, the most commonly used polymers being cellulose, polyacrylamide, nylon, polystyrene, polyvinyl chloride or polypropylene. The solid supports can be in the form of tubes, beads, discs or microplates, or any other surface suitable for conducting an immunoassay. Binding reagents can be linked to the substrate by covalent crosslinking. The binding processes generally entail cross-linking covalently binding or physically adsorbing the molecule to the insoluble carrier.

Labels for use in such assays include enzymes, fluorophores or radionuclide containing molecules (ie. radioisotopes). In the case of an enzyme immunoassay, an enzyme is conjugated to an antibody, generally by means of glutaraldehyde or periodate. Commonly used enzymes include horseradish peroxidase, glucose oxidase, β-galactosidase and alkaline phosphatase, amongst others. The substrates to be used with the specific enzymes are generally chosen for the production, on hydrolysis by the corresponding enzyme, of a detectable colour change. It is also possible to employ fluorogenic substrates, which yield a fluorescent product. Alternatively, fluorescent compounds, such as fluorescein, $Eu^{3+}$ or other lanthanide metals, and rhodamine, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in ELISA, a fluorescent labelled antibody is allowed to bind to the first antibody-hapten complex. After washing off the unbound reagent, the remaining complex is then exposed to the light of the appropriate wavelength, the fluorescence observed indicates the presence of the hapten of interest. Other reporter molecules, such as chemiluminescent or bioluminescent molecules may also be employed.

VII. Binding Reagents for Use in Protein Assay Formats

The above binding assays are typically performing using antibodies as the binding reagents. Antibodies can be polyclonal or monoclonal. The production of non-human monoclonal antibodies, eg., murine, rat and so forth, is well known and may be accomplished by, for example, immunising the animal with a preparation containing an analyte polypeptide (eg., a saposin, LAMP-1 or α-glucosidase) or an immunogenic fragment thereof, optionally with an adjuvant. Antibody-producing cells obtained from the immunised animals can be immortalised and screened for the production of an antibody which binds to analyte. See Harlow & Lane, Antibodies, A Laboratory Manual (C.S.H.P. NY, 1988) (incorporated by reference in its entirety for all purposes). Human and humanised antibodies can also be made but are not superior to rodent antibodies for in vitro diagnostic assays. Intact antibodies and their binding fragments, such as Fv, Fab and (Fab')$_2$ can be used in the present methods.

Other suitable binding reagents can be screened from random libraries of peptides or other compounds can also be screened for suitability. Combinatorial libraries can be produced for many types of compounds that can be synthesised In a step-by-step fashion. Such compounds include polypeptides, β-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, eg., Devlin, WO 91/18980.

IX. mRNA Assays

Alternatively, or additionally to protein analyses, the invention provides methods of diagnosis based on detection and quantification of mRNA encoding saposins, LAMP-1 or α-glucosidase, or amplification products thereof. RNA transcript for analysis is isolated from a biological sample obtained from a biological tissue or fluid in which the gene of interest is expressed. Samples include sputum, blood, blood cells (eg., white cells), tissue or fine needle biopsy samples, urine, peritoneal fluid, and pleural fluid, or cells therefrom. Methods of isolating total mRNA are described in Chapter 3 of Laboratory Techniques in Biochemistry and Molecular Biology: Hybridisation With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridisation With Nucleic Acid Probes, Part I. Theory and Nucleic Acid Preparation, P. Tilssen, ed. Elsevier, N.Y. (1993)).

Frequently, it is desirable to amplify RNA prior to hybridisation. The amplification product can be RNA or DNA, single-stranded, or double-stranded. In one procedure, mRNA can be reverse transcribed with a reverse transcriptase and a primer consisting of oligo dT and a sequence encoding the phage T7 promoter to provide single stranded DNA template. The second DNA strand is polymerised using a DNA polymerase. After synthesis of double-stranded cDNA, T7 RNA polymerase is added and RNA is transcribed from the cDNA template. Successive rounds of transcription from each single cDNA template result in amplified RNA. Alternatively, cDNA can be amplified to generate double stranded amplicon, and one strand of the amplicon can be isolated, ie., using a biotinylated primer that allows capture of the undesired strand on streptavidin beads. Alternatively, asymmetric PCR can be used to generate a single-stranded target. Optionally, amplification product is labelled either in the course of amplification or subsequently. A variety of different fluorescent labels are available including fluorescein and phycoerythrin.

RNA or amplification products thereof are typically detected by hybridisation to a complementary probe. Either the analyte or probe can be labelled. In some assay formats, the analyte is immobilised, and in other formats the probe. Optionally, probes for multiple analytes can be immobilised on the same support and multiple analytes detected and quantified simultaneously. Methods for analysis and quantification of transcript using probe arrays are described in detail in WO 96/14839 and WO 97/01603.

X. Methods of Diagnosis and Monitoring

The analyses of levels of saposins, LAMP-1 and α-glucosidase described above have at least two principal applications. First, such analyses are useful in diagnosing patients who have not already been unequivocally characterised as having a lysosomal storage disease. Analysis of the levels of saposins, LAMP-1 and α-glucosidase provides an indication that a patient suffers from such a disease, or is susceptible to or at risk of such diseases. The relative levels of the different markers can also sometimes provide an indication that a particular lysosomal storage disorder or subset of disorders is present (see Table 1).

TABLE 1

| Disease | A | B | C | D | LAMP-1 | α-glu |
|---|---|---|---|---|---|---|
| Cystinosis | + | ○ | ++ | ++ | ND | + |
| Fabry disease | ++ | + | + | + | ○ | ○ |
| Galactosialidosis | ○ | ○ | ○ | ○ | ++ | − |
| Gaucher's disease | ++ | ++ | ++ | ++ | ++ | ++ |
| GM-I-gangliosidosis | ++ | ○ | + | + | ++ | ○ |
| I Cell | + | ○ | ++ | ++ | ++ | ND |
| Krabbe disease | + | ○ | ○ | ○ | ○ | + |
| α-Mannosidosis | ○ | ○ | ○ | + | ++ | + |
| Metachromatic Leukodystrophy | ○ | ○ | ○ | + | ○ | ○ |
| MPS I | + | ○ | ++ | ++ | ++ | ○ |
| MPS II | + | ○ | ++ | ○ | ++ | + |
| MPS IIIA | ○ | ○ | ○ | ○ | ++ | + |
| MPS III | ○ | ○ | ○ | ○ | ++ | ○ |
| MPS IIIC | ○ | ○ | ○ | ○ | ++ | + |
| MPS IIID | ○ | ○ | + | ○ | ++ | + |
| MPS IVA | + | ○ | ○ | ○ | ++ | − |
| MPS VI | + | ○ | + | + | ++ | ○ |
| Multiple Sulphatase Deficiency | ○ | ○ | ++ | ++ | ++ | ++ |
| Neuronal Ceroid Lipofuscinoses | ○ | ○ | ○ | ○ | ND | ND |
| Niemann-Pick (A/B) | ++ | ++ | ++ | ++ | ○ | + |
| Niemann-Pick(C) | ++ | ○ | ++ | ++ | ○ | + |
| Pompe's disease | ○ | + | + | ++ | ○ | − |
| Sandhoff's disease | ++ | + | + | ○ | ++ | + |
| Sialic Acid Storage disease | + | ○ | ++ | ○ | ○ | ++ |
| Tay-Sachs Type 1 | + | ○ | ○ | ○ | + | + |
| Tay-Sachs (A/B) | ○ | ○ | ○ | ++ | ++ | ++ |
| Wolman disease | + | ○ | ++ | ++ | + | ND |

Table 1 shows correlations between the various lysosomal storage disorders and the four saposin markers, Lamp-1 and α-glucosidase. The symbol ++ indicates a strong positive correlation (ie., at least 80% of subjects with the disorder have a level of marker of at least the 95th percentile of a control population). The symbol + indicates a lesser but still positive correlation (ie., at least 40% of subjects with the disorder have a level of marker of at least the 95th percentile in a control population. The symbol "−" indicates a negative correlation between marker levels and presence of disease. The symbol "○" is used for other measured levels. The symbol "ND" means not determined.

The Table shows that Gaucher's disease is the only one of the lysosomal storage disorders to show strong positive correlations with all six markers tested. A number of diseases showed a strong positive correlation for at least one saposin and for Lamp-1. These disease were, in addition to Gaucher's disease, GM-I-gangliosidosis, I cell disease, MPS I, MPS II, multiple sulphatase deficiency, Sandhoff disease and Tay-Sachs disease (A/B). Several of the diseases showed a strong positive correlation for at least one saposin and not for LAMP-1. These diseases were Niemann-Pick (A/B) and C, Pompe's disease and sialic acid storage disease. Other diseases showed a strong positive correlation for Lamp-1 and not for any saposin. These diseases included galactosialidosis, α-mannosidosis, MPS IIIA, MPS IIIB, MPS II, MPS IIIC, MPS IIID, MPS IVA, and MPS VI. Thus, by examining the levels of several or all of the markers shown in a patient and comparing with the correlations shown in Table 1 or similar Table it is possible to classify a patient as having a particular disease or subset of diseases.

The above diagnostic tests work by comparing a measured level of analyte in a patient with a baseline level determined in a control population of patients unaffected by a lysosomal storage disorder. A significant departure between the measured level in a patient and baseline levels in unaffected persons signals a positive outcome of the diagnostic test. A departure is considered significant if the measured value falls outside the range typically observed in unaffected individuals due to inherent variation between individuals and experimental error. For example, a departure can be considered significant if a measured level does not fall within the mean plus one standard deviation of levels in a control population. In some methods, a departure between a measured level and control levels is judged significant if the measured level is at least the level of the, $75^{th}$, $80^{th}$ or $95^{th}$ percentile of a control population. In other words, the measured level in the patient occurs in only 50%, 25%, 20% or 5% of normal individuals. If the measured level of an analyte does not differ significantly from baselines levels in a control population, the outcome of the diagnostic test is considered negative.

For saposins and Lamp-1, a positive outcome is typically indicated by measured levels in excess of normal levels. For α-glucosidase, a positive outcome can be indicated by measured levels either in excess or below baselines levels. Whether the measured level of α-glucosidase is above or below baselines levels is indicative of the subtype of lysosomal storage disorder affecting the patient (see Table 1). The extent of departure between a measured value and a baseline value in a control population also provides an indicator of the probable accuracy of the diagnosis, and/or of the severity of the disease being suffered by the patient.

If a diagnostic test gives a positive outcome, the patient is, at minimum, identified as being susceptible to or at risk of a lysosomal storage disorder. The patient is then typically subject to further tests or screening. Such tests or screening can include analyses of additional analytes correlated with lysosomal storage disorders that have not already been tested. Such screening can also include performing biochemical tests for deficiency of enzymes associated with particular lysosomal storage disorders. Such assays are typically performed on urine, blood and skin fibroblasts from patients (Schriver et al., supra). For example, a glucosidase can be assayed using 4-methyl-umbelliferyl-α-D-glucopyranoside as a substrate (see Van der Ploeg et al, Ped. Res. 24: 90-94 (1988)). Further tests can also include monitoring for clinical symptoms of a lysosomal storage disorder, which include one or more of Dwarfism, corneal clouding, hepatosplenomegaly, valvula lesions, coronary artery lesions, skeletal deformities, joint stiffness and progressive mental retardation. Further screening can also include analyses of family history for related family members with lysosomal storage disorders, and/or genetic analyses of DNA encoding enzymes associated with such disorders from the patient for polymorphisms associated with lysosomal storage disorders. (See eg., U.S. Pat. No. 5,266, 459). As a result of one or more of these screening assays, the initial diagnosis based on analyte levels can be confirmed (or otherwise), and the particular lysosomal storage disorder affecting a patient can be identified.

Patients identified as having a particular lysosomal storage disorder are then typically administered a treatment for the disorder. Treatment is typically in the form of enzyme-replacement therapy using the enzyme that is impaired or deficient in a particular disorder. For example, Pompe's disease can be treated with α-glucosidase, as described in copending application U.S. Ser. No. 08/700,760 filed Jul. 29, 1996. As a further example, Gaucher's disease can be treated with glucocendorosidase. (See, eg., U.S. Pat. No. 5,879, 680.)

The second principal application of the methods lies in monitoring the condition of patients receiving treatment for a lysosomal storage disorder. A successful treatment outcome is indicated by return of analytes, such as saposins, Lamp-1, and α-glucosidase, from abnormal levels to or toward normal levels. Typically, such methods measure an initial value for the level of analyte before the patient has received treatment. Repeat measurements are then made over a period of time. If the initial level is elevated relative to the mean level in a control population, a significant reduction in level in subsequent measurements indicates a positive treatment outcome. Likewise, if the initial level of an analyte is reduced relative to the mean in a control population, a significant increase in measured levels relative to the initial level signals a positive treatment outcome. Subsequently measured levels are considered to have changed significantly relative to initial levels if a subsequent measured level differs by more than one standard deviation from the mean of repeat measurements of the initial level. If monitoring reveals a positive treatment outcome, the same treatment regime can be continued, or replaced with a treatment regime with a lower dosage. If monitoring reveals a negative treatment outcome, the previous treatment regime is typically modified, either by using a different therapeutic agent or increasing the dosage of the previous agent.

XII. Diagnostic Kits

The invention further provides diagnostic kits containing reagents for use in the methods described above. Typically, such a kit contains at least one reagent that specifically binds to a saposin, a Lamp or α-glucosidase. Some kits contain multiple reagents specifically binding to different analytes. For example, a kit can include a reagent that specifically binds to a saposin, a reagent that specially binds to Lamp-1 and a reagent that specifically binds to α-glucosidase. Some kits contain multiple different reagents for two or more of the different saposins. For example, some kits contain a reagent that binds to saposin A without binding to other saposins, a reagent that binds to saposin C without binding to other saposins, and a reagent that binds to saposin D without binding to other saposins. The reagents are typically monoclonal or polyclonal antibodies but can be other binding agents as described above. In some kits, binding agent(s) are provided immobilised to a solid phase. Some kits provide binding reagents immobilised to the wells of a microtiter dish. Some kits further include sample(s) of the analyte(s) to be detected by the kit for use in calibration of the kit to correlate levels of signal with concentration of analyte. Some kits also contain one of the labels as described above. For example, the label can be in the form of a labelled anti-idiotypic antibody. Kits typically also include a label or instructions describing how to perform the above-described diagnostic assays, and/or how to interpret the results thereby obtained.

EXAMPLES

1. Saposins as a Marker for Lysosomal Storage Disease

This example shows the suitability of saposins A, B, C and D as a screening marker for LSD by determining the levels of these proteins in plasma samples taken from unaffected and LSD-affected individuals.

Materials and Methods

Patient Samples

Plasma samples used were from samples submitted to the National Referral Laboratory (Women's and Children's Hospital, Adelaide, Australia) for LSD screening and processing for routine biochemistry. Whole blood samples for fractionation studies were obtained from healthy volunteers within the laboratory.

Polyclonal Antibodies

Anti-saposins A, B, C and D polyclonal antibodies were produced and characterised as previously described [15]. Each antibody was purified on a 2-mL Hitrap™ Protein G column (Pharmacia Biotech, Uppsala, Sweden) and quantified by absorbance at 280 nm (absorbance=1.4 for 1.0 g/L).

Europium Labelling of Polyclonal Antibodies

Purified anti-saposin polyclonal antibodies were labelled with $Eu^{3+}$ lanthanide, using the DELFIA® labelling kit (Wallac, North Ryde, Australia). Labelled antibodies were purified on a 1.5×30 cm Superose 12 fast-phase liquid chromatography column (Pharmacia Biotech, Uppsala, Sweden) as previously described [13]. The amount of $Eu^{3+}$ conjugated to each antibody molecule was determined by the fluorescence of a known antibody concentration compared to a 1 nM $Eu^{3+}$ standard solution.

Preparation of Calibrators and Quality Control Standards

Liquid calibrators for the immunoquantification of saposins were prepared using purified saposin A, B, C and D proteins [20]. Purified saposin A protein was diluted in DELFIA® assay buffer to obtain final concentrations of 2.43, 1.21, 0.61, 0.3 and 0.15 µg/L. For the saposin A immunoquantification assays, low and high quality control standards were prepared by diluting saposin A protein to 0.24 and 2.43 µg/L, respectively. Purified saposin B protein was diluted in the same buffer to obtain final concentrations of 6.78, 3.34, 1.67, 0.83, and 0.42 µg/L. For the saposin B immunoquantification assays, low and high quality control standards were prepared by diluting saposin B protein to 0.67 and 6.78 µg/L, respectively. Purified saposin C protein was diluted to obtain final concentrations of 1.88, 0.94, 0.47, and 0.24 µg/L. For the saposin C immunoquantification assays, low and high quality control standards were prepared by diluting saposin C protein to 0.47 and 1.88 µg/L, respectively. Purified saposin D protein was diluted to obtain final concentrations of 0.92, 0.46, 0.23, and 0.11 µg/L. For the saposin D immunoquantification assays, low and high quality control standards were prepared by diluting saposin D protein to 0.23 and 0.92 µg/L, respectively.

Calibrators and controls for saposins C and D were supplemented with an equal volume of control plasma sample to that being assayed, to compensate for the inhibitory effects of plasma on the saposins C and D assays. All liquid saposin calibrators and controls were stored at 4° C.

Immunoquantification of Saposins

Determination of saposins was performed using time-delayed fluorescence immunoassays. The basis of this form of assay has been outlined previously [13]. Microtiter plates (Immulon 4; Dynatech Labs., Chantilly, Va.) were coated overnight at 4° C. with anti-saposin polyclonal antibody (2.5 mg/L diluted in 0.1M $NaHCO_3$, pH8.8, 100 µL/well) and pre-washed (×1) with DELFIA® wash buffer. Samples were diluted in DELFIA® wash buffer (100 µL/well), shaken for 10 min at 20° C. and incubated (4 h at 4° C.). Plates were then washed (×6), Eu-labelled anti-saposin polyclonal antibody added (0.25 mg/L diluted in DELFIA® assay buffer, 100 µL/well) and incubated (overnight at 4° C.). The plates were washed (×6), then DELFIA® enhancement solution (200 µL) was added to each well, and the plates shaken (10 min at 2° C.). The fluorescence was read on a Wallac 1234 DELFIA® Research Fluorometer. For each saposin assay, the corresponding saposin calibrators were located across the first row of the microtiter plate with the quality controls dispersed randomly. All saposin calibrators, quality controls and samples were assayed in duplicates. Saposin concentrations were calculated using linear regression.

Fractionation of Whole Blood

Whole blood samples, from 6 control individuals, were fractionated into plasma, white cells and red cells as previously described [21].

Results

Optimisation of Saposin Immunoquantification Assays

Europium labelling of anti-saposin polyclonal antibodies gave recoveries ranging from 75-100% with 4-7 $Eu^{3+}$ atoms bound to each antibody molecule. The final parameters of the immunoquantification assays were optimised by generating a series of calibration curves under different conditions tested. The parameters that were optimised included the concentrations of the coating antibodies and the Eu-labelled antibodies, and the incubation times of the antibodies and samples. Minimisation of cost, time, as well as the reproducibility of each assay was considered when selecting the final assay conditions.

Figure 1:
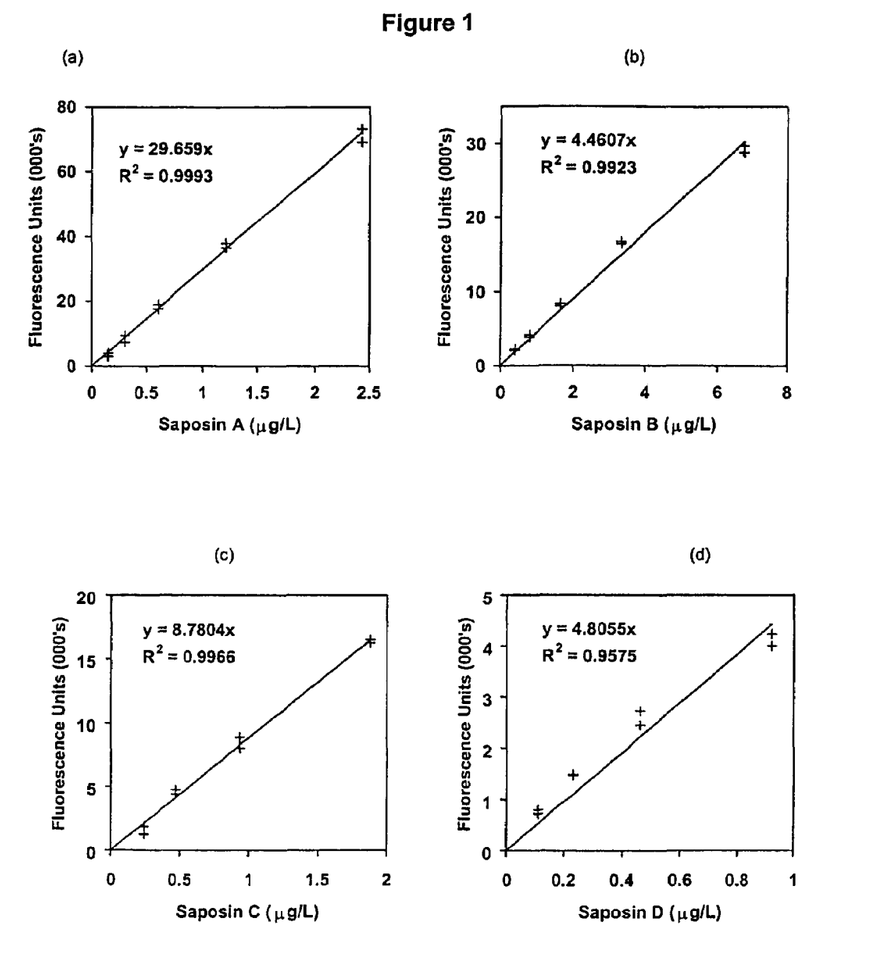
FIG. 1. Calibration curves for saposins A, B, C and D immunoquantification assays. Optimum immunoquantification conditions were used to generate saposin A (panel a), saposin B (panel b), saposin C (panel c) and saposin D (panel d) calibration curves for use in the immunoquantification of the respective proteins. Microtiter plates were coated with primary anti-saposin polyclonal antibody (2.5 mg/L, 4° C., overnight), standards were incubated (4° C., 4 h) and detected with Eu-labelled anti-saposin polyclonal antibody (0.25 mg/L, 4° C., overnight).

The optimised saposins A, B and C calibration curves gave linear responses over the standard range ($R^2$ values>0.99), however, the saposin D calibration curve had a reduced linear range ($R^2$=0.9575) (FIG. 1). When control plasma was added to the saposins C and D calibration curves, a reduction in signal intensity was observed, 2 µL of plasma gave a 20% reduction. To compensate for the inhibitory effect of plasma on the saposins C and D immunoquantification assays, control plasma at an equal volume to that being assayed was added to the calibrators. The assumption was made that LSD-affected plasma would inhibit the assays in the same manner as control plasma, therefore only control plasma was used to spike the calibrators.

Saposin Levels In the Plasma of Control and LSD-Affected Individuals

Figure 2:
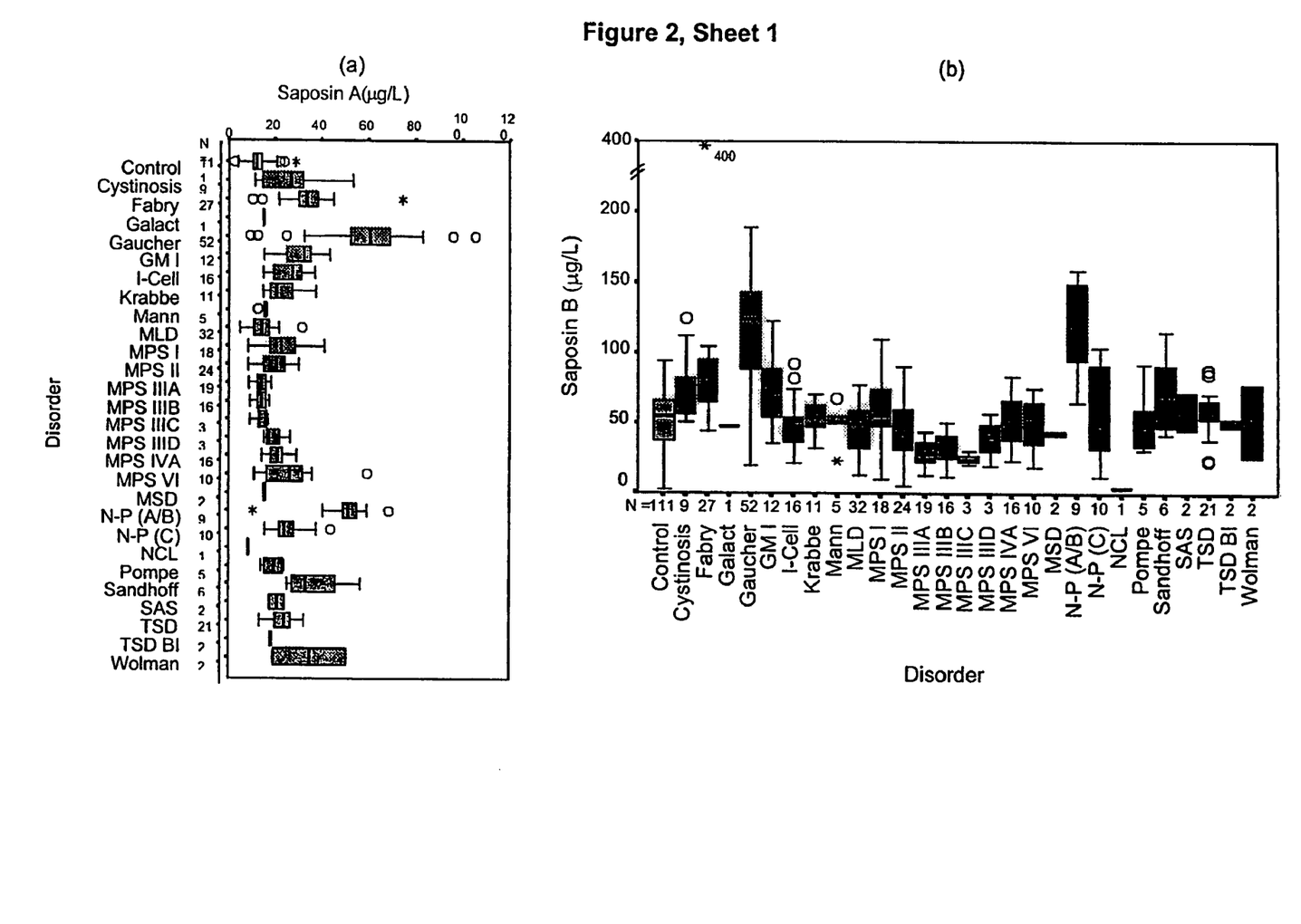

To evaluate the suitability of each of the saposins as markers for newborn screening for LSD, the levels of saposins A, B. C and D were determined in the plasma samples from 111 control individuals (median age=7, range=0-66) and 334 LSD-affected individuals, representing 28 different disorders (Table 1). The $95^{th}$ centiles of saposin concentrations in the control population are listed in Table 1, together with the total proportion of LSD-affected individuals having plasma saposin elevated above this level. The levels of saposins A, C and D showed a tight distribution in the plasma samples of the control population, whereas a wider range of saposin B levels were observed (FIG. 2). A significant proportion of LSD-affected individuals was found to have saposin levels above the $95^{th}$ centile of the control population with some individuals having elevations of up to 10-fold the median concentration of the control population. 15 of the 28 disorders had >80% of individuals with one or more saposin levels above the $95^{th}$ centile of the control population.

TABLE 2

Saposins levels in plasma from control and LSD-affected individuals.

| Disorder | n | Age[a] | | Saposin Levels[b]/(% elevation)[c] | | | | | | |
|---|---|---|---|---|---|---|---|---|---|---|
| | | | | A | | B | | C | | D |
| Control | 111 | 7 | (0-66) | 12.2 | (20.2)[d] | 54.8 (84.5)[d] | | 14.6 | (25.5)[d] | 23.8 (39.1)[d] |
| Cystinosis[e] | 9 | 6 | (1-24) | 26.7 | (56) | 57.7 | (22) | 32.6 | (89) | 49.9 (89) |
| Fabry disease[e] | 27 | 27 | (4-47) | 33.9 | (93) | 82.5 | (48) | 29.3 | (67) | 37.9 (48) |
| Galactosialidosis | 1 | 16 | | 15.1 | (0) | 48 | (0) | 15.2 | (0) | 25.1 (0) |
| Gaucher disease | 52 | 19 | (0-73) | 60.3 | (96) | 124.2 | (81) | 100.2 | (94) | 127.7 (96) |
| GM I-gangliosidosis | 12 | 3 | (0-15) | 32.5 | (83) | 72.3 | (33) | 28.1 | (67) | 35.4 (42) |
| I-Cell disease | 16 | 7 | (0-25) | 27.3 | (69) | 47.5 | (6.3) | 53.3 | (94) | 122 (94) |
| Krabbe disease[e] | 11 | 0.4 | (0.1-0.5) | 20.6 | (63) | 54.1 | (0) | 22.3 | (19) | 41.1 (38) |
| α-Mannosidosis | 5 | 4 | (3-5) | 15.9 | (0) | 51 | (0) | 21.9 | (0) | 35.4 (40) |
| Metachromatic Leukodystrophy[e] | 32 | 5 | (0-11) | 14.1 | (16) | 49.5 | (0) | 19.7 | (9.4) | 38.1 (44) |
| MPS I | 18 | 4 | (0-29) | 23 | (67) | 56.2 | (17) | 39.2 | (83) | 47.9 (83) |
| MPS II | 24 | 3 | (0-11) | 20.6 | (54) | 42.7 | (4.2) | 32.4 | (96) | 37.1 (38) |
| MPS IIIA | 19 | 5 | (1-17) | 14.4 | (0) | 29 | (0) | 21.9 | (21) | 30.9 (16) |
| MPS IIIB | 16 | 6 | (2-21) | 14.3 | (0) | 35 | (0) | 24.1 | (31) | 31.6 (13) |
| MPS IIIC | 3 | 12 | (6-20) | 16.1 | (0) | 24.5 | (0) | 16.6 | (0) | 28.2 (0) |
| MPS IIID | 3 | 2 | (0-3) | 17.2 | (33) | 40.7 | (0) | 27.3 | (67) | 29.8 (0) |
| MPS IVA | 16 | 7 | (1-44) | 21.2 | (63) | 50.1 | (0) | 20.7 | (25) | 32.3 (38) |
| MPS VI | 10 | 5 | (0-16) | 26.6 | (70) | 55.3 | (0) | 29.6 | (60) | 38 (50) |
| Multiple Sulphatase Deficiency | 2 | 7 | (7) | 16.1 | (0) | 43.8 | (0) | 30 | (100) | 43.2 (100) |
| Neuronal Ceroid Lipofuscinoses[e] | 1 | 4 | (4) | 8.6 | (0) | 4.7 | (0) | 20.3 | (0) | 21.5 (0) |
| Niemann-Pick disease (A/B)[e] | 9 | 26 | (2-44) | 51.5 | (89) | 121.2 | (89) | 141.7 | (100) | 163.9 (100) |
| Niemann-Pick disease (C)[e] | 10 | 13 | (0-40) | 24.2 | (80) | 49.3 | (30) | 50 | (100) | 82.2 (90) |
| Pompe disease[e] | 5 | 0.3 | (0.1-0.5) | 19.5 | (40) | 44.7 | (20) | 26.8 | (60) | 43.9 (80) |
| Sandhoff disease | 6 | 1 | (0.9-1.3) | 33.5 | (100) | 71.4 | (50) | 31.5 | (67) | 35.8 (33) |
| Sialic Acid Storage disease | 2 | 2 | (0-3) | 20.9 | (50) | 59.6 | (0) | 36.5 | (100) | 38.2 (0) |
| Tay-Sachs disease type 1[e] | 21 | 4 | (0-27) | 24.1 | (71) | 59.6 | (9.5) | 23.7 | (48) | 35.4 (33) |
| Tay-Sachs disease (A/B) | 2 | 7 | (6-8) | 18.8 | (0) | 50.8 | (0) | 16.7 | (0) | 47.2 (100) |
| Wolman disease[e] | 2 | 0.6 | (0.5-0.8) | 35 | (50) | 52.5 | (0) | 114.8 | (100) | 110.5 (100) |
| Total LSD Patients[d] | 334 | | | | (59) | | (25) | | (61) | (57) |

[a]Median age (range) of individuals within the group.
[b]Median saposin concentrations of individuals within the group (μg/L).
[c]Percentage of individuals within the group with saposin concentration above the 95th centile of the control population.
[d]Saposin concentration at the 95th centile (μg/L).
[e]Disorders that were not elevated with LAMP-1 and LAMP-2.

All saposin assays included low and high quality control standards in order to determine the inter-assay coefficient of variation for each assay performed with the number of replicates ranging from 17 to 24. The coefficient of variation of the saposin A assays for both the low and high quality control standards were <10%. Saposins B, C and D assays gave coefficient of variations of <10% for the high quality control standards and 15-20% for the low quality control standards. A separate experiment was carried out where 24 replicate samples of the high and low standards were assayed on a single plate in order to calculate the intra-assay coefficient of variation. Values ranging from 6-16% were obtained for the low quality control standards and <10% was obtained for the high quality control standards.

As LAMP-1 levels in the same plasma samples had previously been assayed [13], direct comparisons between the levels of saposins and LAMP-1 could be carried out. Using Pearson correlation, strong correlations between all saposins ($p<0.01$) were observed, with the exception of saposin B which showed low correlation with both saposin C and D levels (Table 3). Weak correlations were observed between saposins and LAMP-1 ($p<0.05$) and no correlations were seen between saposin concentrations and the age in the control population.

TABLE 3

Pearson correlation of saposins and LAMP

| | Saposin A | Saposin B | Saposin C | Saposin D | LAMP-1 |
|---|---|---|---|---|---|
| LAMP-2 | 0.316[a] | 0.101[b] | 0.394[a] | 0.341[a] | 0.863[a] |
| LAMP-1 | 0.220[a] | 0.025 | 0.271[a] | 0.273[a] | |
| Saposin D | 0.782[a] | 0.540[a] | 0.921[a] | | |
| Saposin C | 0.827[a] | 0.574[a] | | | |
| Saposin B | 0.745[a] | | | | |

[a]Correlation is significant at the 0.01 level (2-tailed).
[b]Correlation is significant at the 0.05 level (2-tailed).

Saposin Levels in Whole Blood

Whole blood samples from six unaffected individuals were fractionated and the distribution of saposins was determined in plasma, white cells and red cells (Table 3). It was found that the dominant saposin in whole blood was saposin D at a concentration of 75 μg/L, while a greater proportion of saposin B (77%) was found in the plasma fraction as compared to the other saposins. Saposins A, C and D distributions in plasma, white cells and red cells were relatively equal.

TABLE 4

Saposin Levels and Distribution in Fractionated Blood

Average Saposin Levels[a] (% of whole blood)[b]

| Blood Fraction | A | B | C | D |
|---|---|---|---|---|
| Whole Blood | 19.0 ± 2.9 | 25.0 ± 8.3 | 40.4 ± 7.5 | 75.3 ± 12.9 |
| Plasma | 7.2 ± 2.1 (38) | 19.2 ± 8.0 (77) | 9.4 ± 4.5 (23) | 22.6 ± 11.1 (30) |
| Red Cells | 6.8 ± 0.9 (36) | 3.2 ± 0.5 (13) | 17.8 ± 2.0 (44) | 33.4 ± 8.1 (44) |
| White Cells | 4.9 ± 0.7 (25) | 2.5 ± 0.4 (10) | 13.2 ± 2.5 (33) | 19.3 ± 3.2 (26) |

[a]average saposin levels +/− standard deviation
[b]percentage of saposin in whole blood present in each fraction Discussion In 59% of patients, saposin A was found to be elevated above the 95th centile of the control population, and saposins B, C and D were elevated in 25%, 61% and 57% of patients, respectively (Table 1). Of the 28 represented disorders in our study, saposin A levels in 6 groups had >80% of the individuals above the 95th centile of the control group, saposin B was increased in 2 groups, and saposins C and D were each elevated in 10 groups (Table 2). Together the saposins identified greater than 80% of individuals in 15 of the 28 LSD groups, 6 of these were previously not observed to be elevated with LAMP-1 [13], namely Cystinosis, Fabry disease, Niemann-Pick disease (types A/B and C), Pompe disease, and Wolman disease. The remaining LSDs not elevated with Lamp-1 (Krabbe disease, Metachromatic Leukodystrophy, and Tay-Sachs disease) had significant numbers of patients (44-71%) showing increase in saposin levels (Table 2). About 85% of LSD-affected individuals can be detected using both LAMP-1 and saposins as screening markers.

There was a correlation between the LSD groups that store sphingolipids or sphingolipid derivatives and those that showed an increase in saposin levels. For example, Niemann-Pick disease (type A/B) in which sphingomyelin is stored, showed elevations in all saposins. However, of the MPS groups studied only MPS II showed saposin C elevation. Saposins also were not elevated in demyelinating disorders such as MLD and Krabbe disease. The observed elevation of saposins in the various LSD groups may therefore relate to the tissues involved in storage and to the type of substrate stored. Moreover, the degree of saposin increase may also reflect the severity of the individual.

The ratios of individual saposin levels in the plasma from the LSD group were also examined and compared to the control population, in order to determine whether the ratio value was a better LSD detection parameter. However, the strong correlation between the saposins (Table 3) resulted in the ratios of any two saposins giving a lower predictive value than the individual saposins.

Saposin B was by far the most predominant saposin in the plasma of control individuals (Table 2). A greater proportion of saposin B (77%) was found in the plasma fraction compared to saposins A, C and D (38, 23 and 30%, respectively). Saposin D is the dominant saposin in whole blood at 75 µg/L. Because saposins originate from the same precursor, their rate of synthesis should be equal. Thus, the different observed levels probably result from different half-lives, with saposin D having a longer half-life in cells, and saposin B in plasma.

Example 2

Figure 3:
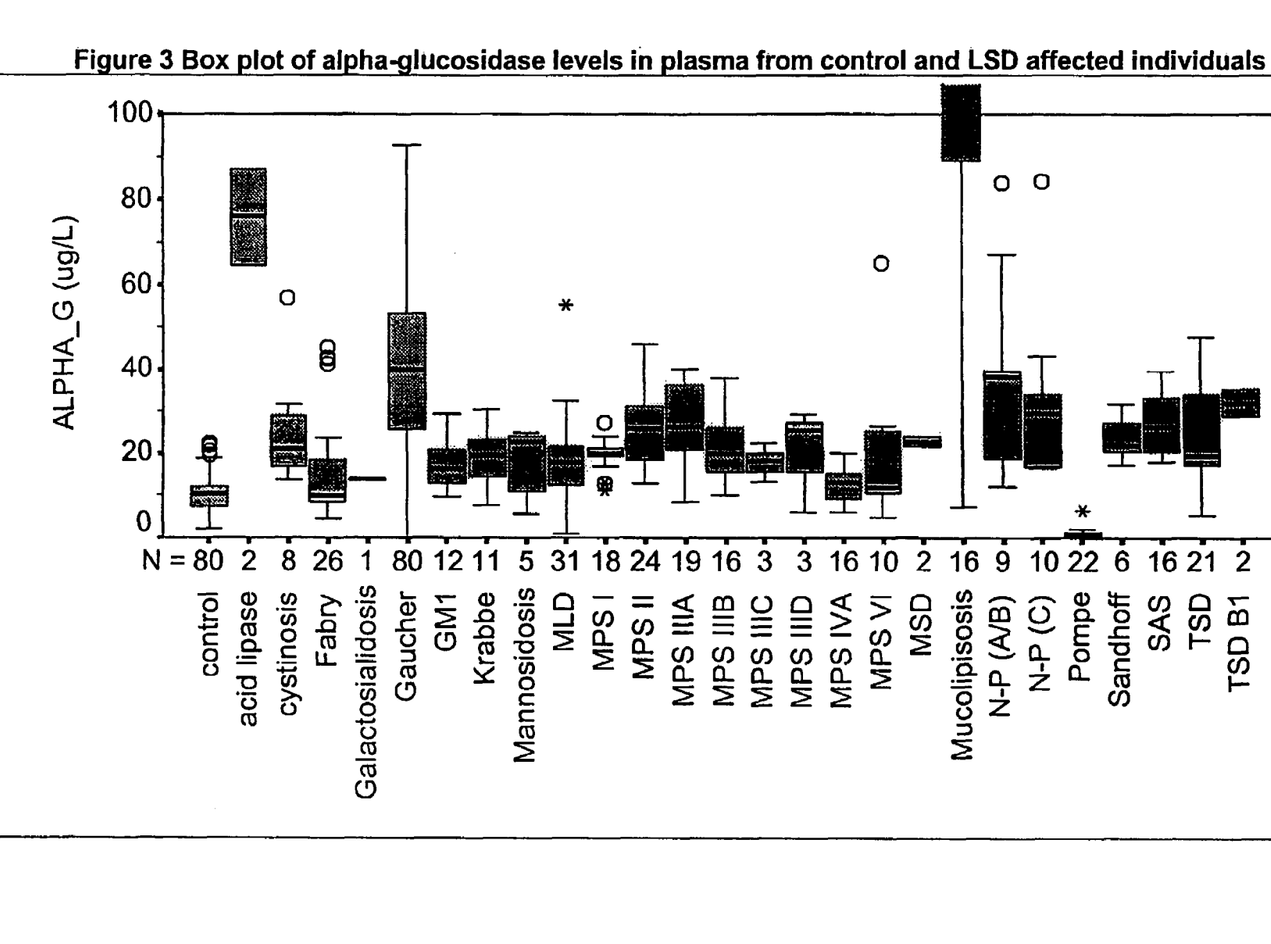

Plasma samples have been assayed for α-glucosidase protein by an immunoquantification assay using the same technology as described for the saposin study. Results are expressed as a box plot in FIG. 3. Results are also presented in Table 5 showing the median level in each disorder group, and the % of patients with an α-glucosidase level elevated above the 95th centile of the control population. Overall 55% of patients showed an elevation of α-glucosidase. All Pompe patients showed a level of α-glucosidase below the 5th centile of the control population.

Therefore, α-glucosidase is a useful marker for the detection of a range of LSD, by detecting either an elevation or a decrease in the level of this protein in plasma serum or whole blood.

TABLE 5

α-glucosidase levels in plasma from control and LSD affected Individuals

| | | | | | | | PERCENTILES | | | | |
|---|---|---|---|---|---|---|---|---|---|---|---|
| | Count | Min | Max | Mean | Std Err | elevated[a] | 05 | 25 | 50 | 75 | 95 |
| control | 80 | 1.9 | 22.3 | 10.4 | .5 | 5 | 3.8 | 7.4 | 10.1 | 12.3 | 20.6 |
| acid lipase | 2 | 64.8 | 87.3 | 76.1 | 11.3 | 100 | | | 76.1 | — | — |
| cystinosis | 8 | 13.5 | 57.2 | 25.6 | 5.0 | 50 | | 15.7 | 21.1 | 30.4 | — |
| Fabry | 26 | 4.5 | 45.5 | 16.2 | 2.5 | 19 | 5.1 | 8.3 | 9.9 | 18.9 | 44.6 |
| Galactosialidosis | 1 | 13.8 | 13.8 | 13.8 | | 0 | 13.8 | 13.8 | 13.8 | 13.8 | 13.8 |
| Gaucher | 80 | .0 | 290.2 | 46.0 | 4.1 | 86 | 11.8 | 25.5 | 40.0 | 53.6 | 92.5 |
| GM1 | 12 | 9.6 | 29.2 | 17.3 | 1.7 | 25 | | 12.1 | 16.3 | 22.0 | — |
| Krabbe | 11 | 7.7 | 30.7 | 19.2 | 2.3 | 45 | | 13.1 | 19.5 | 24.7 | — |
| Mannosidosis | 5 | 5.8 | 24.8 | 17.6 | 3.9 | 60 | | 8.3 | 22.5 | 24.5 | — |
| MLD | 31 | .7 | 55.3 | 18.5 | 1.8 | 29 | 4.0 | 12.1 | 18.0 | 21.8 | 41.7 |
| MPS I | 18 | 11.1 | 27.4 | 19.5 | 1.0 | 39 | 11.1 | 18.7 | 19.8 | 21.6 | — |

TABLE 5-continued

α-glucosidase levels in plasma from control and LSD affected Individuals

| | Count | Min | Max | Mean | Std Err | elevated[a] | PERCENTILES | | | | |
|---|---|---|---|---|---|---|---|---|---|---|---|
| | | | | | | | 05 | 25 | 50 | 75 | 95 |
| MPS II | 24 | 13.0 | 46.1 | 26.3 | 1.8 | 71 | 13.5 | 18.0 | 26.0 | 31.9 | 44.4 |
| MPS IIIA | 19 | 8.4 | 40.1 | 27.0 | 2.2 | 79 | 8.4 | 20.9 | 26.4 | 36.9 | — |
| MPS IIIB | 16 | 10.0 | 38.3 | 21.1 | 1.8 | 44 | | 15.5 | 19.8 | 26.6 | — |
| MPS IIIC | 3 | 13.3 | 22.3 | 17.9 | 2.6 | 33 | | | 18.1 | — | — |
| MPS IIID | 3 | 6.2 | 29.4 | 20.3 | 7.2 | 66 | | | 25.4 | — | — |
| MPS IVA | 16 | 5.9 | 20.2 | 12.3 | 1.0 | 0 | | 9.0 | 13.0 | 15.6 | — |
| MPS VI | 9 | 4.7 | 65.0 | 18.9 | 5.6 | 33 | | 10.2 | 11.9 | 25.7 | — |
| MSD | 2 | 21.5 | 24.2 | 22.9 | 1.3 | 100 | | | 22.9 | — | — |
| Mucolipidosis | 16 | 7.3 | 273.2 | 134.7 | 19.4 | 88 | | 87.1 | 149.1 | 181.2 | — |
| N-P (A/B) | 9 | 12.2 | 84.0 | 38.3 | 7.9 | 67 | | 18.4 | 38.2 | 53.4 | — |
| N-P (C) | 10 | 16.3 | 84.4 | 32.1 | 6.5 | 60 | | 17.0 | 29.4 | 36.6 | — |
| Pompe | 22 | .0 | 6.3 | .9 | .3 | 0 | .0 | .2 | .6 | 1.2 | 5.7 |
| Sandhoff | 6 | 17.4 | 31.6 | 23.5 | 2.1 | 67 | | 19.7 | 22.1 | 28.5 | — |
| SAS | 16 | 18.1 | 39.7 | 26.7 | 1.8 | 88 | | 20.4 | 26.3 | 34.1 | — |
| TSD | 21 | 5.2 | 47.9 | 23.8 | 2.6 | 43 | 5.3 | 17.4 | 19.3 | 34.7 | 47.3 |
| TSD B1 | 2 | 29.0 | 35.2 | 32.1 | 3.1 | 100 | | | 32.1 | — | — |

[a]Percentage of individuals within the group with α-glucosidase concentration above the 95th centile of the control population.

Example 3

The experiment shown in FIG. 2 was repeated for some of the samples using a combination of monoclonal and polyclonal antibodies to saposin C. Microliter plates were coated with the monoclonal antibody 7B2 (4 mg/L, 16 h, 4° C.), washed then incubated with plasma samples (2 μL) in assay buffer (6 h, 4° C.). The plate was washed again, then incubated with solution-phase europium labelled antibodies as indicated at 500 μg/mL (16 h, 4° C.). The plate was washed and developed with enhancement buffer (200 μL/well) and the fluorescence read. Concentrations of saposin C were calculated based on calibration curves using recombinant saposin C.

| Plasma Sample | Detection Antibodies | | |
|---|---|---|---|
| | Poly(EU)[1] | 3A1(Eu)[2] | 3A1(Eu)/Poly(Eu) |
| Control(C2) | 4.5 | 0 | 7.8 |
| Control(C3) | 6.3 | 0 | 11.3 |
| Gaucher(614) | 46 | 0.5 | 41 |
| Gaucher(1500) | 37.5 | 4.4 | 76 |
| MLD(451) | 4.4 | 26 | 36 |
| MLD(552) | 9.4 | 39 | 46 |

[1]Anti-saposin C polyclonal antibody
[2]Anti-saposin C monoclonal antibody

The 7B2 antibody behaved similarly to polyclonal sera in the capture step. However, the 3A1 antibody showed decrease reactivity with control samples, decreased reactivity with Gaucher's disease samples, and increased reactivity with metachromatic leucodystrophy and neuronal ceroid lipofuscinosis samples. These results indicate that there are multiple subtypes of saposin C that are immunologically distinguishable.

The existence of immunologically distinguishable subtypes within the four overall classes of saposins A, B, C and D allows for more sensitive diagnostic assays using monoclonal antibodies specific to a subtype. For example, use of monoclonal antibody 3A1 offers improved sensitivity for detecting elevated levels of saposin C in metachromatic leucodystrophy and neuronal ceroid lipofuscinosis samples relative to controls. Other monoclonals to any of the saposins can be tested for increased sensitivity relative to controls using the procedure described above.

In some methods, a primary screen is performed using polyclonal sera to one or more of the saposins, and samples thereby identified warranting further investigation are subject to a secondary screen with monoclonal antibodies. In some methods, the monoclonal(s) used in the secondary screen are chosen because they exhibit enhanced sensitivity in detecting saposins in a particular disease state suggested by the primary screen. In some methods, a sample is tested with a plurality of monoclonals that bind the same saposin type (eg. saposin C) but specifically bind to different subtypes of this grouping. By using monoclonal antibodies specific to particular subtypes, such as 3A1, it is possible to achieve a higher level of discrimination between signals in diseased and controlled patients increasing the accuracy of the assay.

REFERENCES

1. Hopwood J J, Brooks D A. An introduction to the basic science and biology of the lysosome and storage diseases. In Applegarth D A, Dimmick J E, Hall J G, eds. Organelle Diseases. New York: Chapman & Hall Medical. 1997: 7-35.

2. Neufeld E F, Meunzer J. The Mucopolysaccharidosis. In Schriver C R, Beaudet A C, Sly W S, Valle D, eds. The Metabolic and Molecular Basis of Inherited Disease (Seventh Edition). New York: McGraw-Hill Inc. 1995: Vol. 11, 2465-2494.

3. Markello T C, Bernardini I M, Gahl W A. Improved renal function in children with cystinosis treated with cysteamine. N Engl J Med 1993; 328: 1157-1162.

4. Platt F M, Neises G R, Reinkensmeier G, Townsend M J, Perry V H, Proia R L, et al., Prevention of lysosomal storage in Tay-Sachs mice treated with N-butyldeoxynojirimycin. Science 1997; 276: 428-431.

5. Reuser A J, Kroos M A, Visser W J, Willemsen R. Lysosomal storage diseases: cellular pathology, clinical and genetic heterogeneity, therapy. Ann Biol Clin (Paris) 1994; 52: 721-728.

6. Beutler E, Grabowski G A. Gaucher Disease. In Scriver C R, Beaudet A C, Sly W S, Valle D, eds. The Metabolic and Molecular Basis of Inherited Disease (Seventh Edition). New York: McGraw-Hill Inc. 1995: Vol. 11, 2641-2670.

7. Salvetti A, Heard J M, Danos O. Gene therapy of lysosomal storage disorders. Br Med Bull 1995; 51: 106-122.

8. Gieselmann V. Lysosomal storage diseases. Biochim Biophys Acta 1995; 1270: 103-136.

9. Schuchman E H, Desnick R J. Niemann-Pick disease types A and B: Acid Shphingomyelinase deficiencies. In Scriver C R, Beaudet A C, Sly W S, Valle D, eds. The Metabolic and Molecular Basis of Inherited Disease (Seventh Edition). New York: McGraw-Hill Inc. 1995: Vol. 11, 2641-2670.

10. Crawley A C, Niedzielski K H, Isaac E L, Davey R C, Byers S, Hopwood J J. Enzyme replacement therapy from birth in a feline model of mucopolysaccharidosis type VI. J Clin Invest 1997; 99: 651-662.

11. Taylor R M, Stewart G J, Farrow B R. Improvement in the neurologic signs and storage lesions of fucosidosis in dogs given marrow transplants at an early age. Transplant Proc 1989; 21: 3818-3819.

12. Farrell P M, Aronson R A, Hoffman G, Laessig R H. Newborn screening for cystic fibrosis in Wisconsin: first application of population-based molecular genetics testing. Wis Med J 1994; 93: 415-421.

13. Meikle P J, Brooks D A, Ravenscroft E M, Yan M, Williams R E, Jaunzems A E, et al. Diagnosis of lysosomal storage disorders: evaluation of a lysosome-associated membrane protein LAMP-1 as a diagnostic marker. Clin Chem 1997; 43: 1325-1335.

14. Hua C T, Hopwood J J, Carlsson S R, Harris R J, Meikle P J. Evaluation of the lysosome-associated membrane protein LAMP-2 as a marker for lysosomal storage disorders. Clin Chem 1998; 44: 2094-2102.

15. Leonova T, Qi X, Bencosme A, Ponce E, Sun Y, Grabowski G A. Proteolytic processing patterns of prosaposin in insect and mammalian cells. J Biol Chem 1996; 271: 17312-17320.

16. O'Brien J S, Kishimoto Y. Saposin proteins: structure, function, and role in human lysosomal storage disorders. FASEB J 1991; 5: 301-308.

17. Bradova V, Smid F, Ulrich Bott B, Roggendorf W, Paton B C, Harzer K. Prosaposin deficiency: further characterisation of the sphingolipid activator protein-deficient sibs. Multiple glycolipid elevations (including lactosylceramidosis), partial enzyme deficiencies and ultrastructure of the skin in this generalised sphing. Hum Genet 1993; 92: 143-152.

18. Inui K, Wenger D A. Concentrations of an activator protein for sphingolipid hydrolysis in liver and brain samples from patients with lysosomal storage diseases. J Clin Invest 1983; 72: 1622-1628.

19. Morimoto S, Martin B M, Yamamoto Y, Kretz K A, O'Brien J S, Kishimoto Y. Saposin A: second cerebrosidase activator protein. Proc Natl Acad Sci USA 1989; 86: 3389-3393.

20. Qi X, Leonova T, Grabowski G A. Functional human saposins expressed in *Escherichia coli*. Evidence for binding and activation properties of saposins C with acid β-glucosidase. J Biol Chem 1994; 269: 16746-16753.

21. Kampine J P, Brady R O, Kanfer J N, Feld M, Shapiro D. Diagnosis of gaucher's disease and niemann-pick disease with small samples of venous blood. Science 1967; 155: 86-88.

22. Morimoto S, Yamamoto Y, O'Brien JS, Kishimoto Y. Determination of saposin proteins (sphingolipid activator proteins) in human tissues. Anal Biochem 1990; 190: 154-157.

23. Tayama M, O'Brien J S, Kishimoto Y. Distribution of saposins (sphingolipid activator proteins) in tissues of lysosomal storage disease patients. J Mol Neurosci 1992; 3:171-175.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

The invention claimed is:

1. A method of diagnosing or monitoring susceptibility or at-risk status for a lysosomal storage disorder in a patient comprising:
   a) measuring the level of alpha-glucosidase in a tissue sample from a patient, and
   b) diagnosing susceptibility or at-risk status for a disorder selected from the group consisting of acid lipase disease, mannosidosis, MPSII, MPSIIA, MSD, mucolipidosis, N-P (A/B), N-P (C), Sandhoff, SAS, Gaucher's disease or TSD B1, if the measured level of alpha-glucosidase exceeds the mean level in a control population of individuals not having a lysosomal storage disease;
   wherein the level is an indication of the presence or extent of the disorder in the patient.

2. A method of monitoring treatment of acid lipase disease, mannosidosis, MPSII, MPS IIIA, MSD, mucolipidosis, N-P (A/B), N-P (C), Sandhoff, SAS, Gaucher's disease or TSD B 1, comprising: determining a baseline level of alpha glucosidase in a tissue sample from the patient with the disorder before treatment with an agent; comparing a level of the alpha-glucosidase in a tissue sample from the patient with the disorder after treatment with the agent with the baseline level; wherein a decrease relative to the baseline indicates a positive treatment outcome.

3. A method for assaying a lysosomal enzyme activity present in a tissue sample obtained from a patient comprising:
   (a) combining the tissue sample in a buffer with at least one binding reagent capable of reacting with the lysosomal enzyme present in the tissue sample to form an enzyme reagent complex;
   (b) determining the lysosomal enzyme activity present in the tissue sample from the enzyme reagent complex formed; and
   (c) diagnosing the patient having the lysosomal enzyme activity that is above the mean lysosomal activity of the control population as being susceptible or at-risk for having a lysosomal storage disease comprising: acid lipase disease, mannosidosis, MPSII, MPSIIA, MSD, mucolipidosis, Nieman Pick (A/B), Nieman Pick (C), Sandhoff, SAS, Gaucher's disease or TSD B 1.

4. A method of diagnosing or monitoring a lysosomal storage disorder in a patient comprising:
   a) determining the activity of alpha-glucosidase in a tissue sample from a patient, wherein the activity is an indication of the presence or extent of the disorder in the patient; and
   b) diagnosing susceptibility or at-risk status for a disorder selected from the group consisting of acid lipase disease, mannosidosis, MPSII, MPSIIA, MSD, mucolipidosis, Nieman Pick (A/B), Nieman Pick (C), Sandhoff, SAS, Gaucher's disease or TSD B1, if the determined activity of alpha-glucosidase exceeds the mean activity in a control population of individuals not having a lysosomal storage disease.

5. A method of monitoring treatment of acid lipase disease, mannosidosis, MPSII, MPS IIIA, MSD, mucolipidosis, N-P (A/B), N-P (C), Sandhoff, SAS, Gaucher's disease or TSD B1, comprising: determining a baseline activity of alpha glucosidase in a tissue sample from the patient with the disorder before treatment with an agent; comparing a activity of the alpha-glucosidase in a tissue sample from the patient with the disorder after treatment with the agent with the baseline activity; wherein a decrease relative to the baseline indicates a positive treatment outcome.

* * * * *